United States Patent [19]
Nishiyama et al.

[11] Patent Number: 5,553,496
[45] Date of Patent: Sep. 10, 1996

[54] APPARATUS AND A METHOD FOR DETECTING THE GENERATION OF DUST PARTICLES AND A CLEAN ROOM EQUIPPED WITH THE APPARATUS

[75] Inventors: Hiroaki Nishiyama; Katsuyuki Nakano, both of Kawasaki, Japan

[73] Assignee: Fujitsu Limited, Kanagawa, Japan

[21] Appl. No.: 350,177

[22] Filed: Nov. 30, 1994

[30] Foreign Application Priority Data

Jan. 24, 1994 [JP] Japan ................................. 6-005486

[51] Int. Cl.$^6$ .............................. G01N 15/00; B01L 1/04
[52] U.S. Cl. ...................... 73/432.1; 73/865.5; 454/187
[58] Field of Search .............................. 73/432.1, 31.02, 73/31.03, 28.01, 863.33, 865.5; 454/187; 55/268; 377/6, 19; 340/627, 628; 356/438

[56] References Cited

U.S. PATENT DOCUMENTS

| | | | |
|---|---|---|---|
| 4,475,379 | 10/1984 | Jinotti | 73/28.01 |
| 4,693,175 | 9/1987 | Hashimoto | 55/385 A |
| 5,169,418 | 12/1992 | Honda et al. | 55/268 |
| 5,207,614 | 5/1993 | Passadore | 454/298 |
| 5,259,812 | 11/1993 | Kleinsek | 454/187 |
| 5,369,981 | 12/1994 | Merz et al. | 73/28.01 |

*Primary Examiner*—Hezron E. Williams
*Assistant Examiner*—Helen C. Kwok
*Attorney, Agent, or Firm*—Nikaido, Marmelstein, Murray & Oram LLP

[57] ABSTRACT

For reducing the equipment cost for monitoring dust particles and improving the operation efficiency in a clean room, a plurality of sampling tubes each having a plurality of perforations formed in the side thereof and along the extension thereof are disposed under the floor board of the clean room so as to extend in X and Y directions. The perforations are for sucking the air together with dust particles discharged from the clean room through openings formed in the regions defined in rows and columns on the floor board. The perforations are formed corresponding to each of the region. The sampling tubes are sequentially selected to be connected to laser particle counters dedicated for the X direction and Y direction, respectively, and the dust particles sent via each of the sampling tubes are counted. The generation of dust particles in the clean room is located by associating the measurement data of the dust particles with the order of the sampling tubes in the sequential connection thereof to the laser particle counters.

10 Claims, 8 Drawing Sheets

APPARATUS AND A METHOD FOR DETECTING THE GENERATION OF DUST PARTICLES AND A CLEAN ROOM EQUIPPED WITH THE APPARATUS

TECHNICAL FIELD OF THE INVENTION

The present invention relates to monitoring the cleanness of the atmosphere in a clean room, and in particular, to the improvement of the apparatus and the method for detecting the generation of dust particle in a clean room.

The necessity for forming fine circuit patterns is becoming strong as the density of the semiconductor integrated circuits increase. Such circuit patterns are formed in a clean room which provides an extremely clean environment. Air made clean by filters is sent into the clean room the filters. Monitoring and the control of dust particles floating in the atmosphere in the clean room is conducted so that the density of the dust particles is kept below a predetermined level.

On the other hand, dust particles are generated from the manufacturing or inspection equipment installed in the clean room. Generation of such dust particles changes hour by hour according to the operating conditions of the equipment and the mechanical deterioration chiefly due to the mechanical friction of the member forming the equipment. Therefore, the dust particles floating in the atmosphere in the clean room must always be detected.

DESCRIPTION OF THE RELATED PRIOR ART

For the detection of dust particles in a clean room, a so-called laser particle counter is used in general. The air in the clean room is continually sampled at a constant flow rate, irradiation of a laser beam is applied to the sampled air and light pulses caused by the scattering of the laser beam by the dust particles in the sampled air are counted.

The sampling of the air is carried out as follows:

That is, a number of thin tubes (sampling tubes), each of which has an end connected to the laser particle counter, are set so as to extend up to each of the positions in the clean room, where the air is to be sampled. The air is sucked in each of the sampling tubes through respective another ends of the sampling tubes and sent to the laser particle counter via each corresponding sampling tube.

Figure 10:
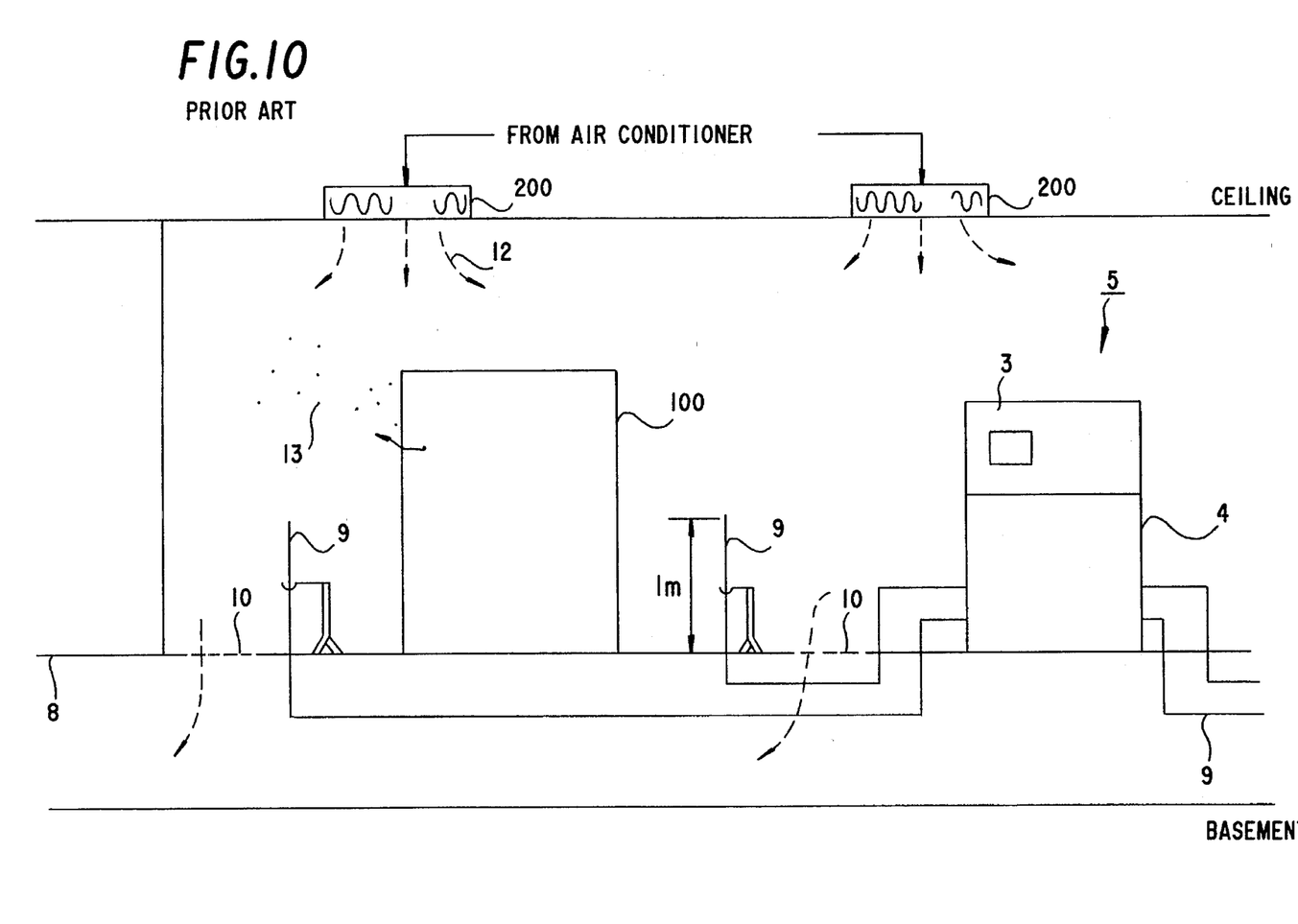
FIG. 10 is a schematic sectional view for explaining a conventional method of monitoring dust particles generated in a clean room.

FIG. 10 is schematic diagram exemplarily illustrating a conventional method for monitoring the generation of the dust particle in a clean room.

Filter 200 is set up in the ceiling of a clean room. Moreover, the floor board 8 of the clean room is provided with openings (through holes) 10, at least one of which openings is formed at each of the regions defined on the floor board 8. The air which is made clean by passing through the filter 200, is sent into the clean room and is then exhausted outside the clean room from openings 10 formed in the floor board 8.

At each of the predetermined positions in a clean room, one of the sampling tubes 9 is arranged so as to vertically project into the clean room through the floor board 8. Each sampling tube 9 extends beneath the floor board 8 in parallel to the floor board 8. One end of each of the sampling tubes 9 is selectively connected to the laser particle counter 3 through a facility 4 for switching the sampling tubes 9. Another end of each sampling tube 9 is opened. Each of the sampling tubes 9 is selected one by one by the switching facility 4 and the air in the clean room is sucked from the opened end of each selected sampling tube 9.

When dust particles are generated from, for example, a manufacturing equipment 100 installed in the clean room, the dust particles are sucked from the opened end of the sampling tube 9 adjacent to the equipment 100 together with the air and carried to the laser particle counter 3. The number of dust particles in the air sent via each of the sampling tubes 9, is counted one by one, and hence, the density of the dust particles (number of dust particles in the unit volume of the sucked air) at each of the positions in the clean room is determined.

In the above-mentioned conventional method, each of the sampling tubes 9 has been set so that the opened end thereof is at a height of about 1 meter from the upper surface of the floor board 8. This is because the semiconductor wafers are often handled while exposed at positions in a clean room, which are one meter high from the surface of the floor board 8 of the clean room. Accordingly, it is considered most effective to monitor the dust particles in the air sampled at this height in a clean room.

As a result, a lot of sampling tubes 9 have necessarily projected from the surface of the floor board 8 into the clean room, corresponding to the positions where the monitoring is required. Therefore, there were the following inconveniences:

1) When a person moves to work in the clean room, the person he is hindered by the projected sampling tubes, and also, if the person or an object moving in the clean room comes in contact with one of the sampling tubes, erroneous location is made due of the generation of the dust particles therefrom; and 2) Relocation or addition of the sampling tubes is needed along with that of the manufacturing or inspection equipment in the clean room, however, such relocation or addition of the sampling tubes is accompanied by substantial difficulties and high cost.

SUMMARY OF THE INVENTION

An object of the present invention is to provide an apparatus and a method for solving the problem in the conventional method.

Another object of the present invention is to provide a clean room which is free from the above-mentioned problems encountered in the conventional method.

In general, the dust particles generated in a clean room are exhausted outside of the clean room together with the air through the openings formed in a region of the floor board, the region being the nearest to the source of the generation of the dust particles in the clean room. Moreover, the air exhausted from the openings can be considered to be in a laminar flow.

Therefore, the inventors of the present invention paid attention to the fact that it is enough to sample the air not in the clean room but immediately after being exhausted outside of the clean room, and the sampling tubes projecting in a clean room as in the conventional method can be eliminated.

Accordingly in the present invention, a plurality of sampling tubes each having a plurality of perforations on the side thereof are arranged along the extention of the sampling tube.

Such sampling tubes are disposed beneath the floor board, adjacent to the floor board and substantially in parallel to the floor board and so as to correspond to respective selected rows or columns defined on the floor board. The perforations of each of the sampling tubes are arranged so as to respectively correspond to selected ones of the regions in each corresponding selected one of the rows or columns defined on the floor board. Each of the regions has at least one of the openings formed therein for exhausting the air in the clean room to the outside, as mentioned above.

The sampling tubes are selected one by one and the air exhausted outside of the clean room from each of the openings formed in the selected regions is sucked into one of the sampling tubes through a corresponding one of the perforations formed in the sampling tube. The dust particles sucked together with the air in each corresponding one of the sampling tubes are sent to a laser particle counter. Thus, the density of the dust particles sent via each of the sampling tubes is measured synchronously with the switching of the sampling tubes.

Since the order of switching the sampling tube can be associated with X coordinates and Y coordinates of the selected rows and columns defined on the floor board, the position where the density of the dust particles is maximum is specified or the distribution of the dust particles in the clean room is detected based on the data regarding the switching order of the sampling tubes and the corresponding data concerning the number of dust particles.

In the above-mentioned conventional method, in order for monitoring the generation of dust particles as to the regions of m rows and n columns defined on the floor board in a clean room, it is necessary to set up m=n sampling tubes. On the other hand, according to the present invention, it is enough to set up m+n of sampling tubes, assuming that the same number of regions are monitored.

DESCRIPTION OF THE PREFERRED EMBODIMENTS

Figures 1, 1A:
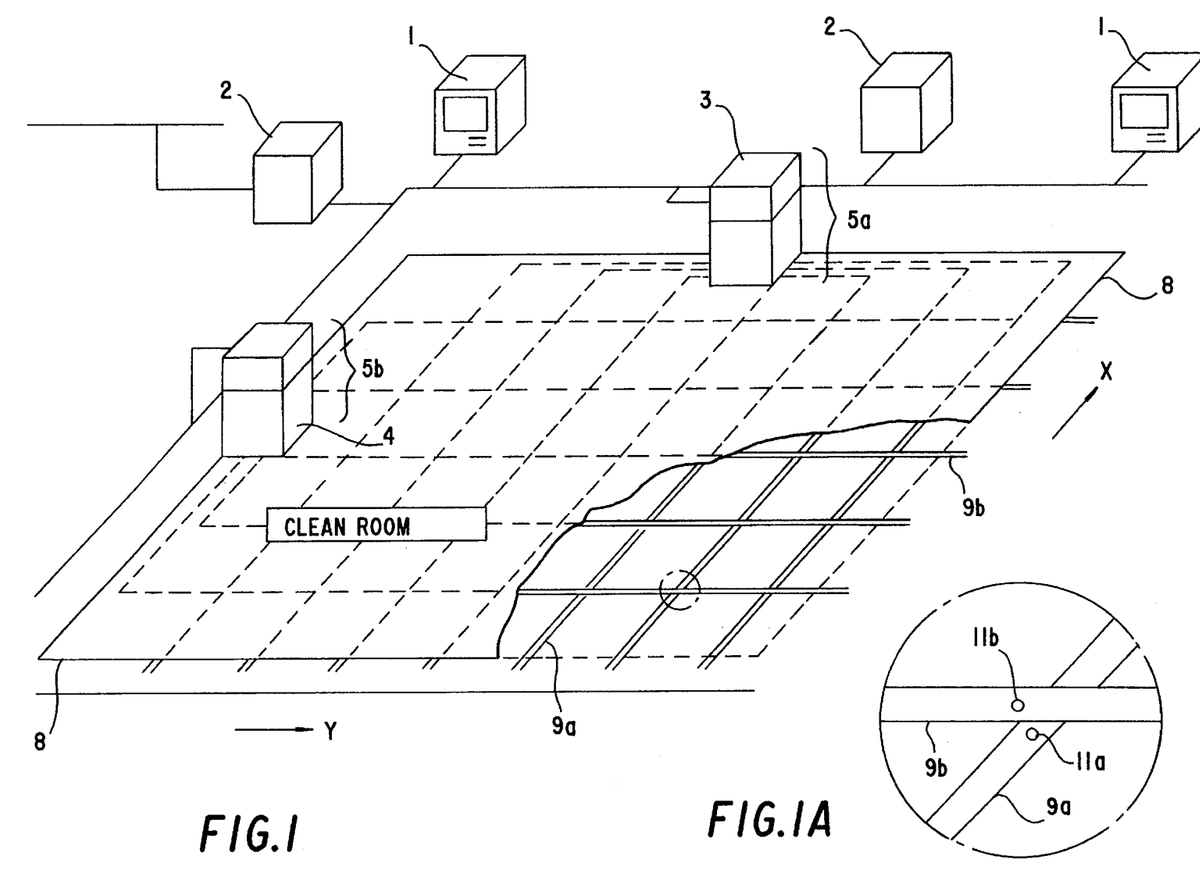
FIGS. 1 and 1A are schematic perspective views of a clean room illustrated for explaining an embodiment of the present invention.

FIGS. 1 and 1A are schematic perspective views for explaining an embodiment of the present invention, illustrating a clean room with the sampling tubes according to the present invention and associated laser particle counters. In FIG. 1, a LAN (local area network) to which the laser particle counters are connected is shown together with the related equipment such as a computer 1 and a server 2, all of which are generally installed outside of the clean room.

Referring to FIG. 1, the floor board 8 of a clean room usually comprises panels of a free-access type, a number of the panels being disposed close to each other. Each of the panels has a size of 60 cm×60 cm, for example. In all or selected ones of the panels in a predetermined area of the floor board 8, including the area in which the equipment 100 is installed and its neighboring area, for example, at least one or generally a plurality of the openings (through holes: not shown in the Figure) each having an aperture of 1 cm$^2$, for example, are formed in each of regions of the floor board 8. The clean air supplied into the clean room from the ceiling is discharged from the clean room outside through these openings formed in the floor board 8. The regions are defined so as to be arranged in rows and columns on the floor board 8.

Respective pluralities of sampling tubes 9a and 9b are disposed under the floor board 8 so as to extend in the directions along the rows and the columns, adjacent to and in parallel to the floor board 8. In FIG. 1, X and Y indicate the directions of the rows and columns, respectively. Each of the sampling tubes 9a and 9b respectively passes under corresponding ones of rows and columns of the regions. Therefore, sampling tubes 9a and 9b intersect under these regions. As shown in the enlarged partial view in FIG. 1A, perforations (sampling holes) 11a and 11b are formed on the sides of the sampling tubes 9a and 9b, respectively, at the intersection of the sampling tubes 9a and 9b.

An end of each of the sampling tubes 9a and 9b is connected to a corresponding one of X axis sensor unit 5a and Y axis sensor unit 5b each comprised of a laser particle counter 3 and a switching facility 4 such as described later. Another end of each of the sampling tubes 9a and 9b is air-tightly closed or is drawn to be thin so as to have a diameter the same as that of the sampling holes 11a and 11b.

Figure 2:
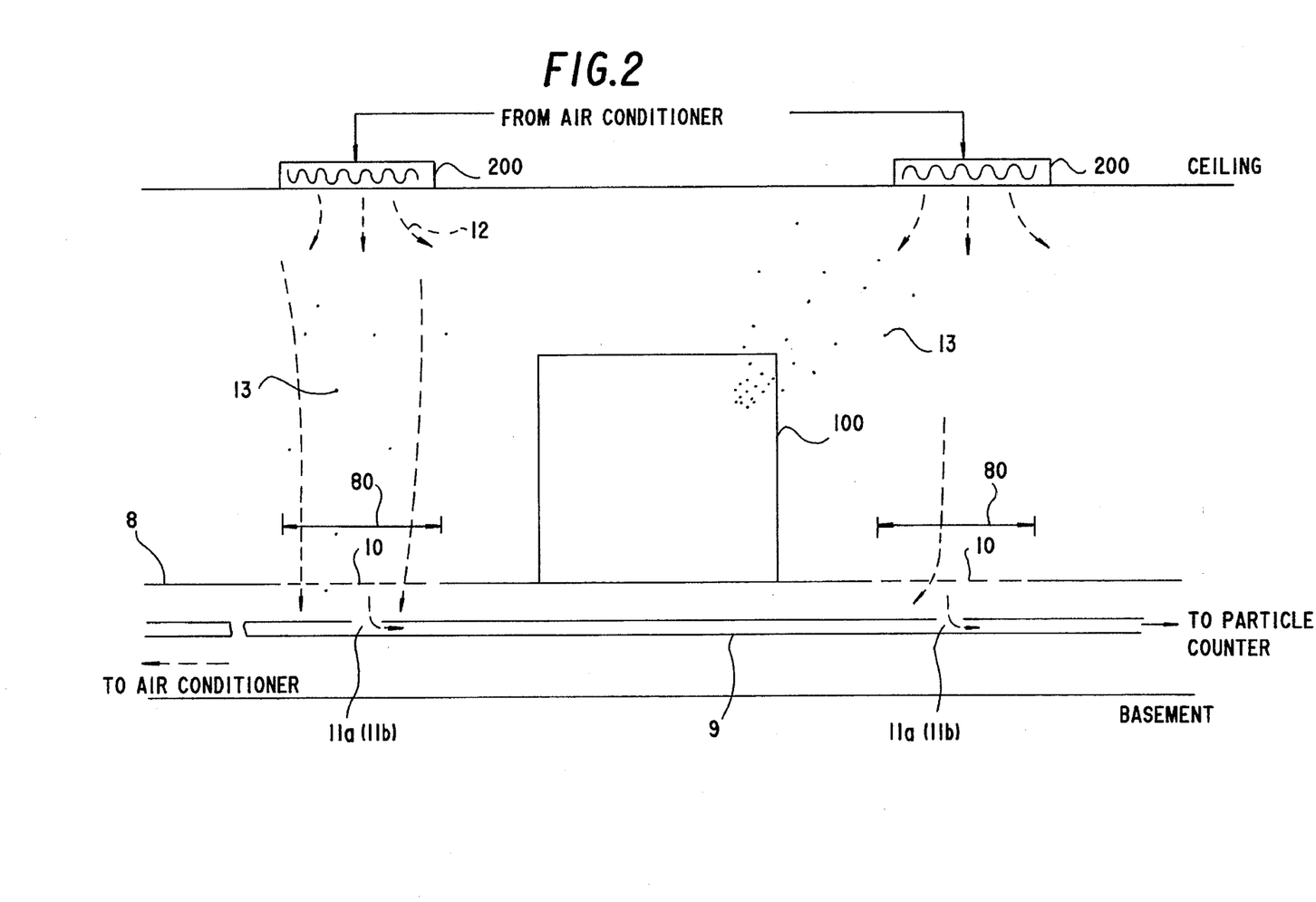
FIG. 2 is a schematic sectional view of a clean room showing the arrangement of the floor board and a sampling tube according to the present invention.

FIG. 2 is a schematic sectional view of a clean room showing the arrangement of the floor board 8 and a sampling tube 9 according to the present invention, taken by perpendicularly cutting the floor board 8 with a plane in parallel to the sampling tube 9. In FIG. 2, the same reference numerals designate the similar or corresponding parts in FIG. 1, and the reference numeral 80 indicates the regions defined on the floor board 8, where at least one of above-mentioned openings (through-holes) 10 is formed.

Installed on the floor board 8 is equipment 100 such as manufacturing or inspection equipment which generate dust particles 13. Dust particles 13 are carried toward the floor board 8 by the flow of air 12 supplied from the ceiling through filter 200 and are discharged outside of the clean room together with the air through the openings 10 formed in the floor board Dust particles 13 discharged outside of the clean room are sucked together with the air in the sampling tube 9a (or 9b) from a corresponding one of the sampling holes 11a (or 11b). Dust particles 13 sampled at each of the regions 80 in the clean room are sent to the sensor unit 5a (or 5b) via the corresponding sampling tube 9a (or 9b) and the number thereof per unit volume of the air is measured for every sampling tube 9a and 9b.

Figure 3:
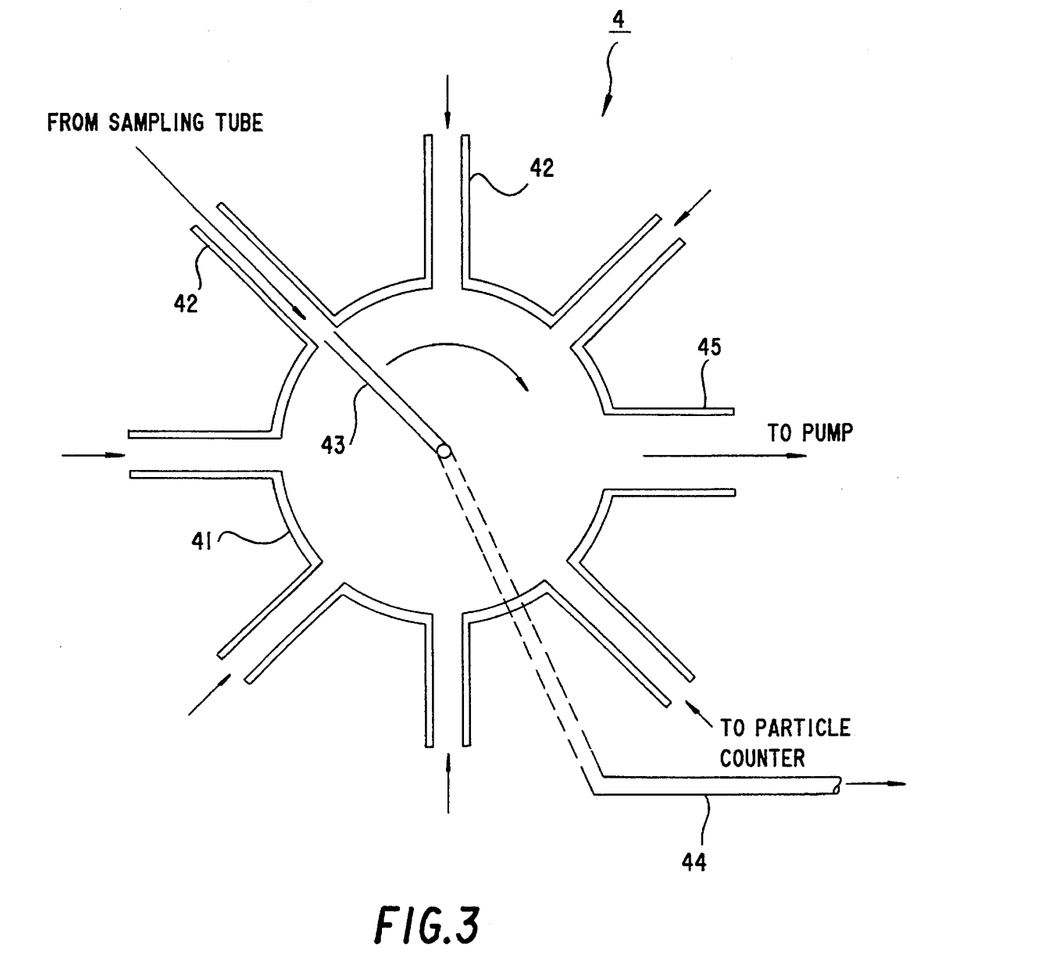
FIG. 3 is a plan view showing the structure of an exemplary facility used for switching the sampling tubes in the present invention.

FIG. 3 is a plan view showing an exemplary structure of facility 4 associated with each of the sensor units 5a and 5b for switching the sampling tubes in the present invention. Such switching facility 4 is well-known and other type of conventional switching facilities having a structure different from FIG. 3 may be employed in the present invention.

The switching facility 4 of FIG. 3 has a cylinder 41 and a number of ports 42 attached on the side of a cylinder 41, the ports 42 being respectively connecting the sampling tubes 9a or 9b. Both of the upper end and lower end of the cylinder 41 are airtightly sealed off.

A tubular member 43 which is supported rotatable around the central axis of the cylinder 41 is installed in the cylinder 41. One end the tubular member 43 slidably contacts with the inner surface of the cylinder 41. Another end of the tubular member 43 is airtightly connected to a pipe 44 with a known rotational sealing mechanism (not shown in the FIG). The pipe 44 is fixed to the cylinder 41. Another end of the pipe 44 is connected to the aforementioned laser particle counter 3. In response to the rotation of the tubular member 43, each of the sampling tubes 9a (or 9b) is selected one by one and the air sucked in each selected sampling tube 9a (or 9b) is separately sent to the laser particle counter 3.

The number of the dust particles sent together with the air via each selected sampling tube 9a (or 9b) is counted. The air flowing into the cylinder 41 from the sampling tubes 9a (or 9b) in a period when these sampling tubes are not selected is exhausted outside though a duct 45 by a not-shown supplementary exhausting system.

Each of the selected sampling tubes 9a and 9b can be identified, according to the rotation angle, for example, of the tubular member 43 in the switching facility 4 of FIG. 3. Therefore, it is possible to locate the generation of dust particles in a clean room, by identifying respective ones of sampling tubes 9a and 9b corresponding to the respective maximum values of the density of dust particles.

The procedure of detecting the position where dust particles are generated in a clean room according to the present invention is explained in detail with reference to FIG. 4.

Figure 4:
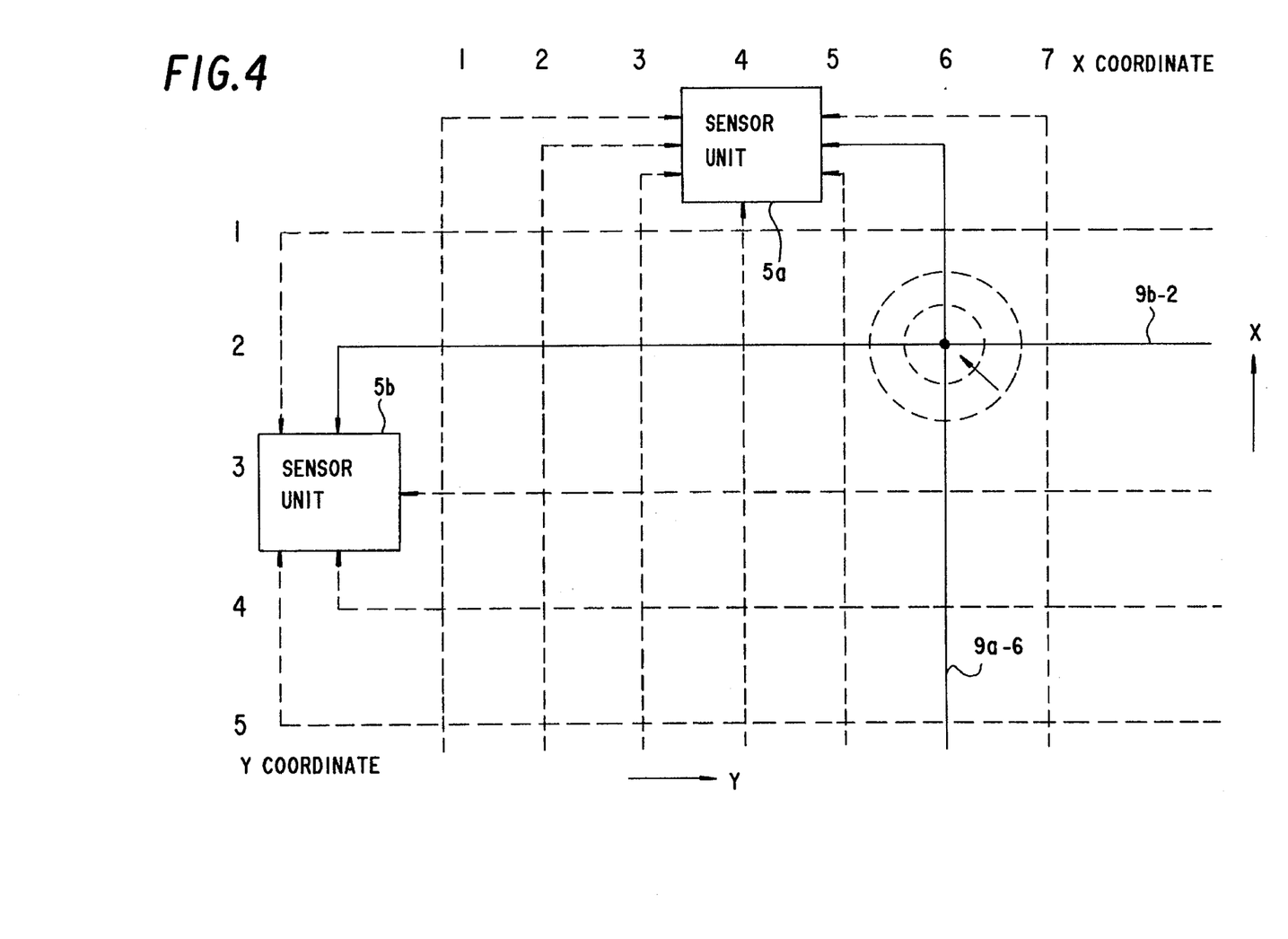
FIG. 4 is a plan view for explaining the method of locating the generation of dust particles according to the present invention.

In FIG. 4, a first group of sampling tubes 9a extending in parallel to the X direction are connected with an X-axis sensor unit 5a and a second group of sampling tubes 9b extending in parallel to the Y direction are connected with Y-axis sensor unit 5b. Strictly speaking these sampling tubes 9a and 9b are connected with respective switching facilities 4 built into the sensor units 5a and 5b.

The respective cycles of switching the first group of sampling tubes 9a and the second group of sampling tube 9b by the switching facilities 4 does not have to be identical. For instance, when the number of the first group of sampling tubes 9a is assumed to be m, the switching cycle of the second group of sampling tubes 9b may be set to m times larger than that of the first group of sampling tubes 9a.

Figure 5:
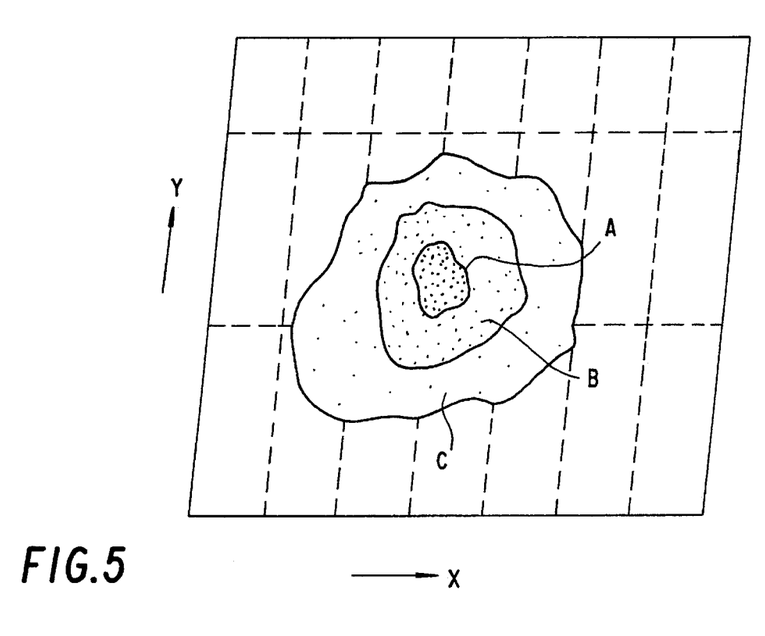
FIG. 5 is a plan view showing an exemplary schematic distribution of dust particles generated in a clean room.

The distribution of dust particles generated from a position in a clean room usually shows an almost concentric circle, as shown in FIG. 5. The density is the highest at the central part A and lowers gradually in the order of B and c.

Assuming that dust particles generated at a position nearest to the point having X,Y coordinates (6,2), for instance, the respective maximum densities are detected by the sensor units 5a and 5b when the sampling tubes 9a-6 and 9b-2 are selected. The detection values obtained when other sampling tubes are selected decrease more and more toward the respective both sides of the sampling tubes 9a-6 and 9b-2.

If dust particles are generated concurrently at three or more positions in a specific relation with each other, such as positions respectively having X,Y coordinates (2,2) and (6,4), for the position having X,Y coordinates (6,2), for example, it is obviously impossible to distinguish these positions from each other.

However, it is seldom that dust particles are generated from three or more different positions at the same time in a clean room. Moreover, the probability that the respective coordinates of these positions are in the relation as mentioned above is so small as to be negligible. Therefore, it is possible to locate the generation of dust particles in a clean room, according to the present invention.

In the above embodiment, the first group of sampling tubes 9a extending in parallel to the X direction and the second group of sampling tubes 9b extending in parallel to the Y direction as shown in FIG. 1 are connected to corresponding individual switching facilities 4, respectively. It may use a sensor unit common to the sampling tubes 9a and 9b. However, a larger delay of the detection timing between the first group of sampling tubes 9a and the second group of sampling tubes 9b may occur in that case. Therefore, it is necessarily required that some errors due to the timing delay should be permitted for the location of the generation of dust particles or the sampling tubes 9a and 9b be switched at a higher switching speed.

Further, a configuration may be used where the sampling tubes 9a or 9b are exclusively disposed so as to correspond to respective ones of selected rows or columns of the regions each having the openings 10, and the perforations 11a or 11b in the side of each of the sampling tubes 9a or 9b are exclusively formed so as to correspond to respective ones of the regions in each of the selected rows or columns.

The perforations (sampling holes) 11a (or 11b) formed in the side of each of the sampling tubes 9a (or 9b) are arranged in a straight line along the extention of each sampling tube. Therefore, the distance from each sampling hole 11a (or 11b) to the sensor unit 5a (or 5b) is not the same. As a result, the head loss between each sampling hole 11a (or 11b) to the sensor unit 5a (or 5b) is different. Accordingly, if all of the sampling holes 11a (or 11b) in each sampling tube 9a (or 9b) have a size the same as each other, the respective flow rates of the air sucked from the sampling holes 11a (or 11b) are different from each other. This means that a faulty detection might be caused on locating the generation of dust particles in a clean room, since the number of dust particles counted by the laser particle counter is proportional to the flow rate of the air.

Figure 6:
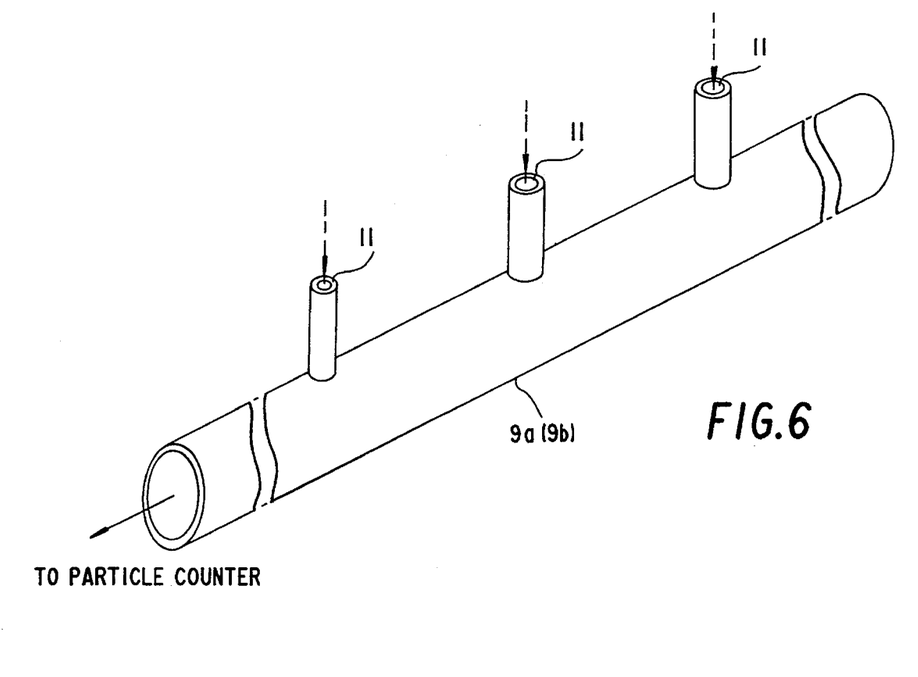
FIG. 6 is a schematic perspective view showing an exemplary structure of the sampling tube according to the present invention.
Figure 7:
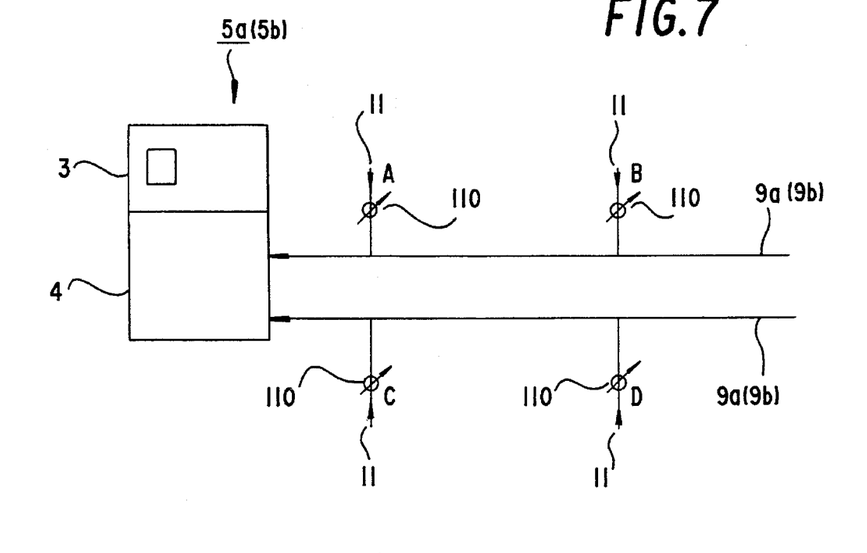
FIG. 7 is a schematic block diagram showing another exemplary structure of the sampling tube according to the present invention.

FIG. 6 and FIG. 7 are a schematic perspective view and a schematic block diagram, respectively, each showing a corresponding exemplary structure of the sampling tube according to the present invention, where means to eliminate the faulty detection based on the reason mentioned above is provided.

Referring to FIG. 6, each of the sampling tubes 9a (or 9b) is provided with a plurality of sampling holes 11a (or 11b) each being a cylinder, for example, having a smaller diameter the nearer to the above-mentioned sensor unit 5a (or 5b). The aperture of each of the sampling holes 11a (or 11b) is designed so that the flow rates of the air sucked therethrough are equal to each other throughout the sampling tubes 9a and 9b.

Referring to FIG. 7, the sampling holes 11 formed in each of sampling tubes 9a (or 9b) have the same size as each other but are provided with corresponding ones of flow-rate-variable valves 110. The valves 110 are adjusted so that the flow rates of the air passing therethrough are equal to each other throughout the sampling tubes 9a and 9b.

Figure 8:
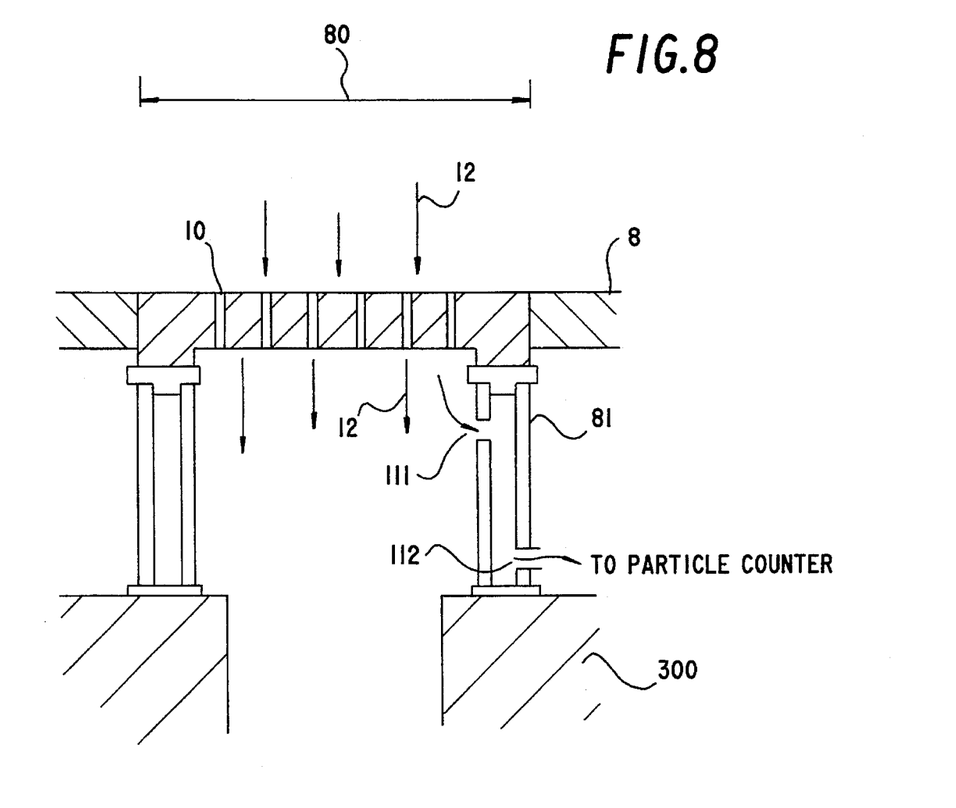
FIG. 8 is a sectional view for explaining another embodiment of the present invention.

FIG. 8 is a sectional view for explaining another embodiment of the present invention, where post 81 supporting the floor board 8 of free access type is used for sampling dust particles discharged under the floor board 8. The post 81 is usually a hollow cylindrical member. In the present invention, the posts 81 are each installed under a corresponding one of regions 80 of the floor board 8, in which the above-mentioned openings 10 are formed.

At the upper and the lower sides of each post 81, perforations 111 and 112 are formed, respectively. The upper perforation 111 is used as the sampling hole 10 and the lower perforation 112 is connected with the above-mentioned sampling tube 9a or 9b (not shown in the figure). Reference numeral 300 in FIG. 8 denotes a foundation supporting the posts 81. By providing each of the posts 81 with a couple of the lower perforations 112, respective ones of lower perforations 112 of posts 81 corresponding to every two neighboring regions 80 in each of above-mentioned selected rows or columns may be interconnected by a tube similar to the sampling tube 9a or 9b. Thus, dust particles sucked together with the air through the upper perforation 111 of each of the posts 81 are sent to the above-mentioned sensor unit 5a (or 5b).

An individual tube may be installed for connecting the lower perforation 112 of each post 81 to the sensor unit 5a (or 5b). In this configuration, the tubes equal in number of the sampling tubes in the conventional method are needed, however, there is an advantage that the tubes do not project in a clean room though the floor board 8 like in the conventional method.

The present invention is effective for other purposes than that of determining the two-dimensional coordinates of the source of dust particles generating in a clean room. For instance, one of the sampling tubes 9a having sampling holes 11 formed therein as described above is set up in parallel to equipment such as a belt conveyer which substantially extends in a one-dimensional direction. According to this configuration, there is no need to set up a number of individual sampling tubes at the positions along the equipment, where generation of dust particles is monitored. Dust particles can surely be detected by the single sampling tube, upon generating at any of the positions situating along the equipment.

In general, the generation of dust particles is monitored at every 50 m² areas on the floor of a clean room. Therefore, monitoring of 100 areas is carried out in a clean room having a floor area of about 5000 m². Since the number of sampling tubes which can be connected with the above-mentioned switching facility built in the sensor unit is about 30, 100 sampling tubes and about 4 laser particle counters have been needed for monitoring the clean room in the conventional method.

According to the present invention, it is enough to install about 20 sampling tubes. That is, it is possible to monitor the generation of dust particles at 100 positions by installing about 10 sampling tubes for each of the X and Y directions in a clean room, for instance. The number of necessary laser particle counters is 1 or 2 and each of the switching facilities associated with the laser particle counters is required to permit only about 10 sampling tubes connected thereto, in this case. Thus, since the necessary number of the laser particle counters and the sampling tubes is fewer compared with the conventional method, respectively, the installation cost relating to this equipment is decreased.

Figure 9:
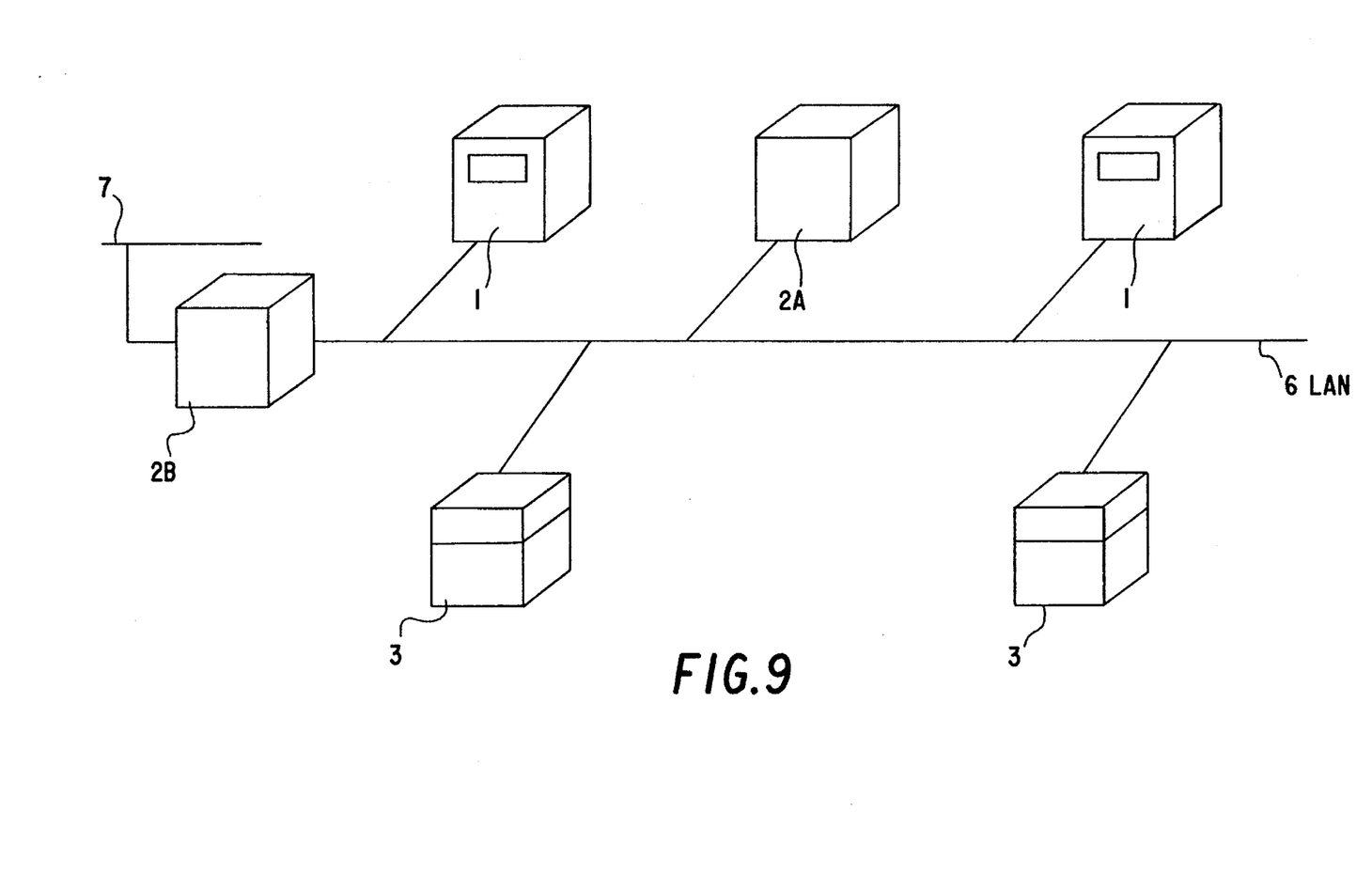
FIG. 9 is a schematic block diagram showing a local area network used in the present invention.

FIG. 9 is a schematic block diagram showing a LAN (local area network) comprising the equipment used in the present invention, the equipment including the above-mentioned sensor units 5a and 5b, and the devices which exchange information with the sensor units 5a and 5b. Measurement data regarding the density of dust particles and control data regarding the order of switching of the sampling tubes by the switching facilities 4 are sent from the sensor units 5a and 5b one by one through LAN 6 and accumulated in one to one correspondence in the server (data storage device) 2A.

Computer 1 sends out information for controlling the switching facility 4 to the sensor units 5a and 5b, and receives the measurement data from server 2A. The exchanges of the data is carried out through LAN 6. Computer 1 associates the measurement data regarding the density of dust particles with the coordinates data derived based on the control data regarding the order of switching of the sampling tubes. Meanwhile, computer 1 compares the measurement data with a reference value and generates an alarm if the value of the measurement data exceeds the reference value.

The network corresponding to a clean room can be connected with a similar network corresponding to other clean rooms or a system for monitoring these networks via a transmission line 7, for instance, through another server 2B (rooter).

Conventionally, the laser particle counters and the switching facilities are separately connected to the computer by individual cables. Accordingly, the clean rooms are congested with cables, and therefore, the traffic of the workers moving in the clean room and the arrangement of the manufacturing equipment and so forth in the clean room are restricted. However, these problems can be solved by the introduction of the LAN and the freedom in the change of the position or additional installation of the manufacturing or inspection equipment is increased.

As described above, the necessary number of equipment including the laser particle counters, sampling tubes and switching facility for connecting the sampling tubes one by one selectively to the laser particle counters, all necessary for locating the generation of dust particles in a clean room can be decreased according to the present invention. Thus the present invention is effective for decreasing the equipment cost of a clean room. Moreover, the present invention is effective for the design concerning the addition or the relocation of the equipment in a clean room and also for reducing the cost accompanied thereby. In addition, since the sampling tubes do not project into the clean room, the movement of workers in the clean room can be facilitated and the reliability of the dust particles measurement can be improved.

In the above description, a clean room for the manufacture of semiconductor devices is taken as an example to be applied with an apparatus or a method of the present invention. However, the present invention may be applied to other clean rooms used for different purposes or fields including manufacture of other electronic devices such as LCD (liquid crystal display), pharmaceutical and biochemical industries and so forth.

What is claimed is:

1. An apparatus for detecting particles which are generated in a space partitioned by walls including a first wall and a second wall facing in parallel to each other, wherein air cleaned in advance is sent into the space from the first wall so as to flow toward the second wall and to be discharged outside of the space through a plurality of openings formed in the second wall, the openings corresponding to each of regions defined on the second wall so as to be arranged in rows and columns, the apparatus comprising:

a plurality of sampling tubes disposed outside of the space so as to be adjacent to the second wall and in parallel to the second wall, said plurality of sampling tubes including a first group of sampling tubes extending so as to correspond to respective rows of openings and a second group of sampling tubes extending so as to correspond to respective columns of openings, wherein each of the sampling tubes has an open end and a plurality of perforations formed on a side thereof so as to correspond to respective regions in at least one of a corresponding row and column;

a counter for counting a number of particles in the air which is discharged outside of the space through the openings corresponding to the regions in each of the rows and the columns, the air being sucked in corresponding sampling tubes through the perforations formed thereon and sent to the counter via a corresponding sampling tube; and a facility for sequentially connecting each of the sampling tubes through the corresponding open end to the counter so that the air sucked in each of the sampling tubes is sent to the counter at a different timing.

2. An apparatus in claim 1, wherein the perforations formed on the side of each of the sampling tubes have respective sizes which are smaller in size nearer to the open end of each corresponding sampling tubes.

3. An apparatus in claim 1, wherein each of the sampling tubes has a plurality of valves connected to respective perforations formed on the side thereof, the valves being set to have respective flow rates which are smaller for the valves nearer to the open end of each corresponding sampling tubes.

4. An apparatus in claim 1, wherein the counter sends out first data for identifying each of the sampling tubes sequentially connected thereto and second data relative to the number of particles in the air sent thereto via each corresponding sampling tubes, the apparatus further comprising:

storing means for accumulating the first data and the second data having one to one correspondence to each other; and a processing unit having accesses to each of the first data and corresponding second data accumulated in the storing means and said processing unit identifying respective sampling tubes of the first group of the sampling tubes and the second group of the sampling tubes, both corresponding to respective maximum values of the number of the particles in the air sent to the counter via the first and second groups of the sampling tubes.

5. An apparatus in claim 4 further comprising a local area network to which the counter, the storing means and the processing unit are connected.

6. An apparatus of claim 1, wherein a set of the counter and the facility for sequentially connecting each of the sampling tubes to the counter is provided for each of the first group of the sampling tubes and the second group of the sampling tubes.

7. An apparatus of claim 1, wherein the perforations formed on the side of each of the sampling tubes of the first group of sampling tubes correspond to a selected one of the regions in a selected one of the rows, respectively, and the perforations formed on the side of each of the sampling tubes of the second group of the sampling tubes correspond to a selected one of the regions in a selected one of the columns, respectively.

8. A clean room partitioned by walls including a ceiling and a floor, wherein air cleaned in advance is sent thereinto from the ceiling so as to flow toward the floor and the air is discharged outside the clean room through a plurality of openings formed in the floor, the openings corresponding to each of regions defined on the floor so as to be arranged in rows and columns, wherein the clean room is equipped with an apparatus comprising:

a plurality of sampling tubes disposed outside of the clean room so as to be adjacent to the floor and in parallel to the floor, said plurality of sampling tubes including a first group of sampling tubes extending so as to correspond to respective rows of the openings and a second group of sampling tubes extending so as to correspond to respective columns of openings, wherein each of the sampling tubes has an open end and a plurality of perforations formed on a side thereof so as to correspond to respective regions in at least one of a corresponding row and column;

a counter for counting a number of particles in the air which is discharged outside of the clean room through the openings corresponding to the regions in each of the rows and the columns, the air being sucked in corresponding sampling tubes through the perforations formed thereon and sent to the counter via a corresponding sampling tube; and a facility for sequentially connecting each of the sampling tubes through the corresponding open end thereof to the counter so that the air sucked in each of the sampling tubes is sent to the counter at a different timing.

9. A method for detecting particles which are generated in a space partitioned by walls including a first wall and a second wall facing in parallel to each other, wherein air cleaned in advance is sent into the space from the first wall so as to flow toward the second wall and to be discharged outside of the space a plurality of openings formed in the second wall, the openings corresponding to one of regions defined on the second wall so as to be arranged in rows and columns with respective predetermined distances therebetween, the method comprising the steps of:

disposing a plurality of sampling tubes outside of the space so as to be adjacent to the second wall and in parallel to the second wall, the sampling tubes including a first group of sampling tubes extending so as to correspond to respective rows of the openings and a second group of sampling tubes extending so as to correspond to respective columns of the openings, wherein each of the sampling tubes has an open end and a plurality of perforations formed on a side thereof so as to correspond to respective regions in at least one of a corresponding row and column;

sequentially connecting each of the sampling tubes to a counter through the corresponding open end so as to send the air to the counter at a different timing, the air being discharged outside of the space through the openings corresponding to the regions in each of the rows and columns and the air being sucked in a corresponding one of the sampling tubes through the perforations formed thereon;

counting a number of particles in the air sent to the counter via a corresponding sampling tube; and determining a position on the second wall, which is regarded as a location where particles are generating, by identifying respective sampling tubes of the first group of the sampling tubes and the second group of the sampling tubes, both corresponding to respective maximum values of the number of the particles in the air sent to the counter via the first and second groups of the sampling tubes.

10. An apparatus for detecting particles which are generated in a space partitioned by walls including a first wall and a second wall facing in parallel to each other, wherein air cleaned in advance is sent into the space from the first wall so as to flow toward the second wall and to be discharged outside of the space through a plurality of openings formed in the second wall, the openings corresponding to each of regions defined on the second wall so as to be arrange in a straight line, the apparatus comprising:

a sampling tube disposed outside the space with an intervention of the wall in between and in parallel to the second wall, wherein the sampling tube has an open end and a plurality of perforations formed on a side thereof so as to correspond to the respectivie regions;

a counter connected through the open end of the sampling tube, said counter for counting a number of particles in the air discharged outside the space through the openings corresponding to the regions, the air being sucked into the sampling tude through the perforations formed thereon and sent to the counter via the sampling tube.

\* \* \* \* \*